United States Patent
Park et al.

(10) Patent No.: US 10,632,007 B2
(45) Date of Patent: Apr. 28, 2020

(54) THERMOPLASTIC CAST HAVING OUTSTANDING DEFORMABILITY AND RIGIDITY, AND PRODUCTION METHOD FOR SAME

(71) Applicant: WOORI MATERIAL INC., Daejeon (KR)

(72) Inventors: Jongchil Park, Daejeon (KR); Seogmyeon Gil, Daejeon (KR)

(73) Assignee: WOORI MATERIAL INC., Daejeon (KR)

( * ) Notice: Subject to any disclaimer, the term of this patent is extended or adjusted under 35 U.S.C. 154(b) by 400 days.

(21) Appl. No.: 15/024,652

(22) PCT Filed: Sep. 23, 2014

(86) PCT No.: PCT/KR2014/008845
§ 371 (c)(1),
(2) Date: Mar. 24, 2016

(87) PCT Pub. No.: WO2015/046863
PCT Pub. Date: Apr. 2, 2015

(65) Prior Publication Data
US 2016/0242949 A1    Aug. 25, 2016

(30) Foreign Application Priority Data
Sep. 24, 2013 (KR) .................. 10-2013-0113371

(51) Int. Cl.
*A61F 5/00* (2006.01)
*A61F 5/058* (2006.01)
(Continued)

(52) U.S. Cl.
CPC .............. *A61F 5/058* (2013.01); *A61F 5/01* (2013.01); *A61L 15/12* (2013.01); *A61L 15/14* (2013.01);
(Continued)

(58) Field of Classification Search
None
See application file for complete search history.

(56) References Cited

U.S. PATENT DOCUMENTS

| 4,143,655 A | 3/1979 | Custer et al. |
| 4,443,511 A * | 4/1984 | Worden ................ A41D 31/02 |
| | | 428/198 |

(Continued)

FOREIGN PATENT DOCUMENTS

KR    10-2008-0029024 A    4/2008

OTHER PUBLICATIONS

Supplementary European Search Report dated Mar. 13, 2017 in application No. 148489453.

*Primary Examiner* — Kim M Lewis
(74) *Attorney, Agent, or Firm* — Maschoff Brennan (57) ABSTRACT

A thermoplastic cast, which is easy to reuse or implant, and a production method for same, are described. The cast includes a core material to which is attached polycaprolactone while being made in a mesh shape by the mutual crossing over and connecting of threads having a predetermined diameter, with the weaving of a plurality of strands of thin threads; and a structure which is made using a polycaprolactone composite and is formed so as to surround the outer part of the core material by means of insert injection. The patient experiences no discomfort despite the cast being structurally robust, because ventilation properties are improved due to the cast being formed in a mesh shape and because the structure, which is made using the polycaprolactone composite, is formed so as to surround the outer part of the core material by means of insert injection.

7 Claims, 12 Drawing Sheets

(51) Int. Cl.
*A61F 5/01* (2006.01)
*A61L 15/12* (2006.01)
*A61L 15/14* (2006.01)
*B29C 45/14* (2006.01)
*B29K 67/00* (2006.01)
*B29K 105/08* (2006.01)
*B29K 105/16* (2006.01)
*B29K 267/00* (2006.01)
*B29K 309/08* (2006.01)
*B29K 509/00* (2006.01)
*B29L 31/00* (2006.01)

(52) U.S. Cl.
CPC .......... *B29C 45/14* (2013.01); *B29K 2067/04* (2013.01); *B29K 2105/0845* (2013.01); *B29K 2105/16* (2013.01); *B29K 2267/003* (2013.01); *B29K 2309/08* (2013.01); *B29K 2509/00* (2013.01); *B29L 2031/753* (2013.01)

(56) References Cited

U.S. PATENT DOCUMENTS

| | | | |
|---|---|---|---|
| 6,673,029 B1* | 1/2004 | Watson | A61F 13/04 602/6 |
| 7,985,192 B2* | 7/2011 | Sheehan | A61F 5/01 602/5 |
| 7,985,195 B2* | 7/2011 | Jennings-Spring | A61F 13/064 602/41 |
| 2011/0224385 A1* | 9/2011 | Shoji | C07D 273/08 525/437 |
| 2011/0244170 A1 | 10/2011 | Hsu et al. | |
| 2015/0305914 A1* | 10/2015 | Wu | A61F 5/01 602/7 |
| 2016/0067103 A1* | 3/2016 | Anthony | A61F 5/37 602/43 |

* cited by examiner

FIG. 1a

(Prior Art)

FIG. 1b

(Prior Art)

THERMOPLASTIC CAST HAVING OUTSTANDING DEFORMABILITY AND RIGIDITY, AND PRODUCTION METHOD FOR SAME

TECHNICAL FIELD

The present invention relates to a thermoplastic cast having outstanding deformability and rigidity, and a production method for the same. More specifically, the present invention relates to a thermoplastic cast which prevents an injured part (affected area) from moving during a treatment process for when an arm, leg, or other body part of a human or animal is fractured or injured, has outstanding deformability such that when being attached to the affected area, a medical procedure may be easily performed, and has a high rigidity after being applied through the medical procedure; and to a production method for the same.

BACKGROUND ART

Typically, when a joint, an arm or a leg is fractured or injured, the injured joint, arm, or leg is fixed using a cast, a plaster cast, or a brace, and the like, to enable a smooth treatment.

Conventionally, to fix such an injured joint, arm, or leg, a bandage and plaster were used to apply a plaster cast, but such plaster is not only heavy, but cannot be reformed after being solidified. Moreover, since the plaster is degraded or damaged when exposed to moisture, it is difficult for the patient to bathe or shower, and there are also disadvantages such as the area on which the plaster cast is applied being poorly ventilated.

Due to such reasons, casts which are not damaged even when taking a bath or shower, or having a structure that allows air to easily pass through are being developed recently, and the thermoplastic mesh shaped body disclosed in U.S. Pat. Nos. 6,673,029 and 4,143,655 is an example thereof.

Figure 1A:
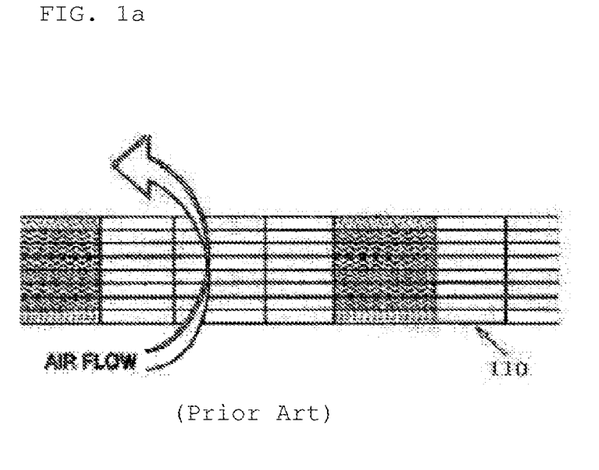
FIGS. 1a and 1b illustrate an embodiment of a conventional cast.
Figure 1B:
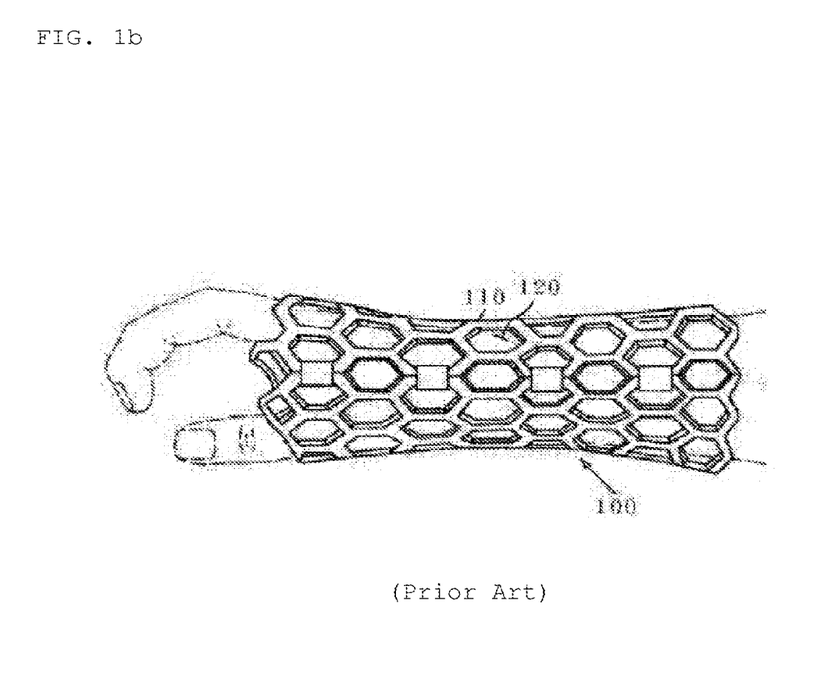

In particular, the mesh shaped body 100 disclosed in U.S. Pat. No. 6,673,029 is made in a mesh shape of which the size of the apertures 120 is relatively large, as illustrated in FIGS. 1a and 1b. Here, to ensure sufficient strength for firmly supporting and protecting a part of the body, the material forming the mesh shape is formed by laminating 6-12 layers of a fiberglass fiber 110 to form a sheet shape, and then cutting this sheet shaped material such that the shape of the apertures form a hexagonal mesh array. With such a cast (mesh shaped body), not only is it difficult to laminate multiple layers of the resin impregnated fiberglass fiber, but when the cast is pulled in order to perform a procedure for applying the cast on a body part of the patient, the sides defining the mesh shape are stretched (hereinafter referred to as "elongation"). Consequently, the thickness of the sides is reduced such that not only is the strength of the cast reduced, but due to excessive elongation of the sides in a lengthwise direction, there is a disadvantage in that the connecting parts are unable to maintain a flat plane, and thus some of the connecting parts protrude sharply in a vertical direction and contact the skin of the patient such that the patient feels discomfort.

Moreover, when multiple layers of the resin impregnated fiberglass fiber are laminated as described above, the surface of the fiber layer becomes unsmooth due to uneven impregnation during the process of impregnating with the resin, and since the patient may feel discomfort due to the cast when wearing the cast consisting of such an unsmooth surface, in order to form a smooth surface a separate layer must be reformed in the area contacting the skin of the patient, and thus the production process is complicated.

Furthermore, even when, as above, the separate layer is formed on the surface contacting the skin of the patient, since the surface of the layer disposed therein is not smooth, the parts laminated thereon may not be smooth, and thus, when the thickness of the layer contacting the skin of the patient is not greater than a predetermined thickness, the patient may continue to experience discomfort.

In addition, in the above patent, in order to produce the cast as a mesh shaped body, after first forming a fabric using the fiberglass fiber, the apertures are created by cutting rhombus shapes from the fabric, and thus strands of the fiberglass fiber may be loosened from the fabric. In this case, the strength of the cast may be weakened, and when the loosened parts of the strands are those impregnated with resin, these parts become pointed and thus irritating the skin of the user is a concern.

It is necessary for a cast or a plaster cast to have sufficient strength in order to maintain a fractured bone in the proper position or to suppress movement in the arms or legs such that treatment is accelerated, swelling in the injured parts of the arms or legs is stabilized, and body parts are protected from impact or injury.

For example, when a bone is fractured, it is advantageous for the strength of the cast in the direction of the body to be high to allow the fractured bone to be maintained in the proper position, and for this reason, the 'geometrically apertured protective and/or splint device comprising a re-mouldable thermoplastic material', in which air passes through open through-holes and which is structured to be high in strength in the longitudinal direction and relatively lower in strength in the circumferential direction, has been proposed in U.S. Pat. No. 7,985,192.

Figure 2A:
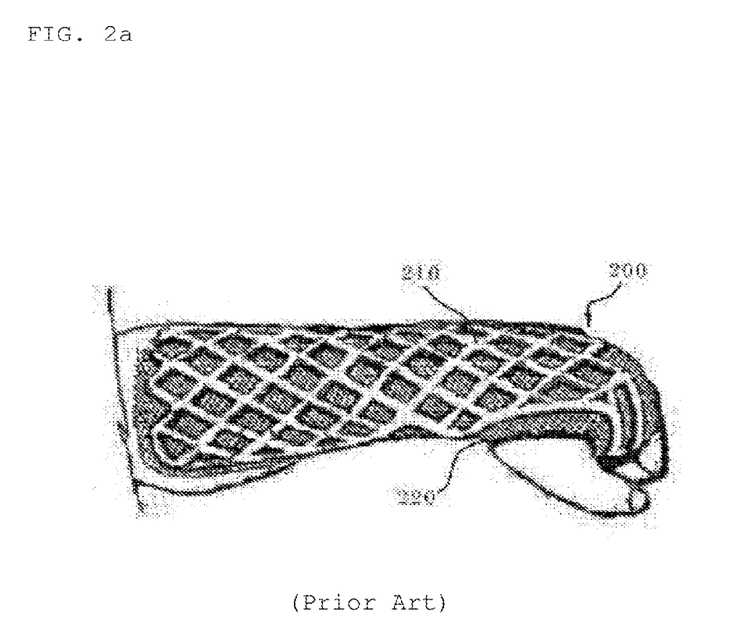
FIGS. 2a and 2b illustrate another embodiment of a conventional cast.
Figure 2B:
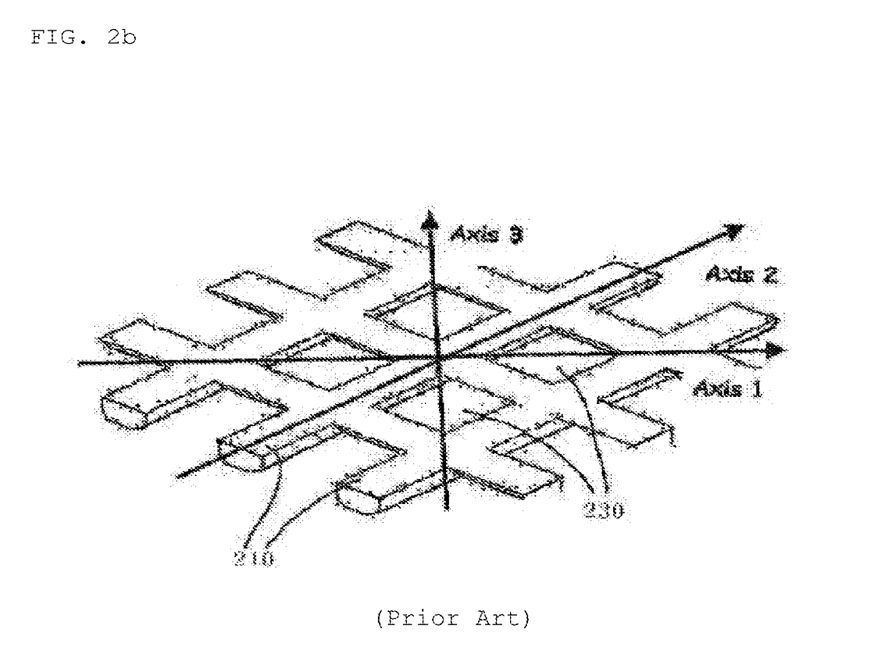

The splint device 200 proposed in the above patent document is composed of a splint member 210 and a spacer member 220, as illustrated in FIGS. 2a and 2b, and here, the splint member 210 is formed as a mesh shaped body such that a plurality of rhombus shaped openings 220 are formed between them, and due to such a structure, by restricting elongation in a lengthwise direction of a side while allowing stretching to be easy in a direction parallel to a first axis and a third axis, the shape of the rhombus formed in the mesh shaped body may be easily deformed (hereinafter, this is referred to as "deformation" so as to be distinguished from "elongation", which indicates stretching of the length of the side), and thereby an attempt was made to reduce the difficulty of the medical procedure.

However, despite the splint device disclosed in the above patent document being easily deformed such that the medical procedure for applying the splint device on a patient is comparatively easy, since the entire cross section of the mesh shaped splint member 210 is formed from a polycaprolactone composite material in which ligno-cellulose is added, not only is the strength relatively weak, but there is a disadvantage in that the elongation in a lengthwise direction of the side may continue to occur such that the thickness of the side decreases and thus weakens the strength thereof.

Therefore, it is necessary to develop a cast in which elongation in a lengthwise direction of the side is restricted during a medical procedure for applying the cast on a body part of the patient to enable the strength of the cast to be maintained, the apertures in the mesh structure are allowed to be easily deformed according to the external shape of the body part of the patient to enable the medical procedure of applying the cast to be easily performed, and the patient does not feel discomfort when wearing the cast; and to develop a production method for the same.

DISCLOSURE

Technical Problem

The present invention was conceived in order to solve the problems of a conventional cast in the form of a mesh shaped body, and it is an objective thereof to provide a thermoplastic cast having sufficient strength and also excellent deformability so as to be easily applied through a medical procedure on a body part of a patient, of which the connecting part of the mesh shaped body does not protrude vertically, even when a force is applied to the cast, such that the patient does not feel discomfort, capable of being mass produced, and having superb deformability and rigidity; and to provide a production method for the same.

Technical Solution

An object of the present invention is to provide a thermoplastic cast having, as above, superb deformability and rigidity, and may be achieved through the thermoplastic cast including a core material to which is attached polycaprolactone and having a mesh shape formed by connecting threads, each of which has a predetermined diameter and is obtained by weaving a plurality of strands of thin yarn, and a structure which is made of a polycaprolactone composite and is formed so as to surround the outer portion through insert injection.

Moreover, another object of the present invention is to provide a production method for a thermoplastic cast having superb deformability and rigidity, in which the cast has a mesh shape and includes a core which is made of a fiber material and to which polycaprolactone is attached, and a structure which is made of a polycaprolactone composite and is formed so as to surround the outer portion of the core material, and is achieved through the production method that includes producing the core material through a mesh shaped body forming step in which a mesh shaped body is formed by mutually crossing threads, each of which has a predetermined diameter and is obtained by weaving a plurality of strands of yarn, and a polycaprolactone attaching step in which polycaprolactone is attached to the mesh shaped body; and producing the structure through a core material shape defining step in which the shape of the core material is defined by inserting, into a shape template, the core material to which polycaprolactone is attached, and a structure forming step in which the structure is formed by injecting the polycaprolactone composite on the outer portion of the core material after the core material of which the shape is defined in the shape defining step is placed inside of a mold.

In the present invention, the core material shape defining step includes installing a guide cap on the upper portion of the shape template, and then, by lowering a pressurizing member while the core material is being placed on the upper portion of the guide cap, inserting the core material in a groove formed in the shape template.

Also, in the present invention, the thread composed of the plurality of strands is a blended yarn in which polyethylene terephthalate fiber is mixed with polycaprolactone fiber.

Moreover, in the present invention, the thread composed of the plurality of strands is a polyethylene terephthalate fiber of which the outer portion is coated with polycaprolactone.

Also, in the present invention, an outer cover made of rubber is formed/attached on the outer portion of the structure through an outer cover forming step which includes any one process among dipping, insert injection, and sheet fusion.

In addition, in the present invention, a fiber reinforced glass fiber or a polyethylene terephthalate fiber is added to the polycaprolactone composite which forms the structure.

Moreover, in the present invention, polyethylene or polyurethane is added to the polycaprolactone composite which forms the structure.

In addition, in the present invention, a groove having an inwardly recessed shape is formed in a portion at which the structures mutually cross each other.

Also, in the present invention, a nucleating agent made of talc is added to the polycaprolactone composite which forms the structure.

Advantageous Effects

In the present invention, a cast is formed as a mesh shape to provide excellent ventilation, and may be easily deformed such that the applicable part of the body of a patient is not limited and also a medical procedure is easily performed.

Moreover, the cast of the present invention is light while also being thinner than a conventional plaster cast, and the like, and thus since a patient equipped with the cast may wear clothing over the cast, being active and using the cast is simple.

Furthermore, in the present invention, since a structure forming the surface of the cast is formed through insert injection, the surface of the cast is smooth, and thus even when contacting the skin of the patient, the patient does not feel discomfort, and also the cast may be mass produced.

Also, in the present invention, since the structure of the cast is made of a thermoplastic resin, a sealed structure for shutting out moisture, and the like, is not required during production, and by being reheated, the cast may be easily corrected when needed, and may also be repeatedly used.

In addition, since the cast of the present invention may be appropriately modified according to the body structure of the patient, the applicable part is not limited, and also, since the strength in the longitudinal direction is greater than the strength in the circumferential direction, the bones, and the like, in the patient may be robustly supported.

Moreover, since the core material composed of the thread is surrounded by the structure made of a polycaprolactone composite, stretching of the core material is limited, while also providing an appropriate elasticity.

Also, in the present invention, since the structure is made of the polycaprolactone composite to which a fiber reinforced glass fiber or a polyethylene terephthalate fiber is added, the strength is excellent and the fractured part may be strongly supported.

In addition, in the present invention, an outer cover made of a low-irritant rubber material is provided such that chemical substances, and the like, forming the cast are prevented from directly contacting the skin of the patient, and a cushioning effect may also be expected, and thus it is not necessary beforehand to wrap a skin protector under the cast in order to protect the skin.

BEST MODE FOR CARRYING OUT THE INVENTION

Hereinafter, the composition and effects of the present invention are described in greater detail through the accompanying drawings illustrating exemplary embodiments thereof.

Figure 3:
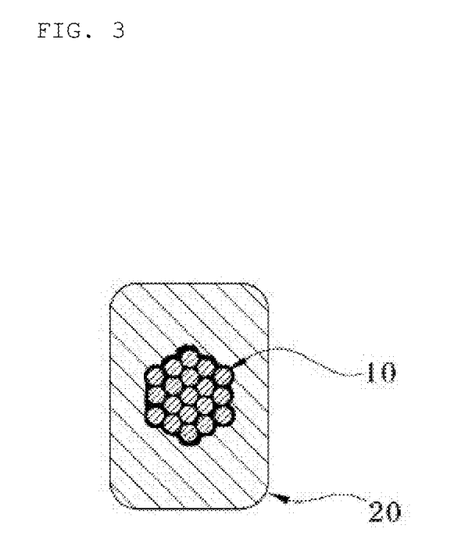
FIG. 3 is a cross-sectional view illustrating an embodiment of a thermoplastic cast according to the present invention.

The present invention relates to a thermoplastic cast used for covering and thereby fixing or correcting a fractured part of a patient and, as illustrated in FIG. 3, the thermoplastic cast according to the present invention is composed of a core material 10 and a structure 20 formed so as to surround the outer portion of the core material and made of a polycaprolactone (PCL) composite.

As illustrated in FIG. 3, the core material 10 is made in a mesh shape (mesh shaped body) by connecting threads, each of which has a predetermined diameter and is obtained by weaving a plurality of strands of thin yarn, and then attaching polycaprolactone on the outer portion of the threads by: impregnating a thermoplastic polycaprolactone with the mesh shaped body, using polyethylene terephthalate (PET) fiber of which the external circumferential surface is coated with polycaprolactone and melting the polycaprolactone coated part with heat, or melting the polycaprolactone fiber included in the mesh shaped body with heat. For this, a common yarn, a blended yarn in which polyethylene terephthalate fiber and polycaprolactone fiber are mixed, or the polyethylene terephthalate fiber of which the external circumferential surface is coated with polycaprolactone is used as the thread forming the mesh shaped body.

In the present invention, as described above, the core material 10 is made of the thread which is composed of the plurality of strands, and thus may be freely formed into various forms, and is also light and not easily damaged.

Moreover, as described above, in the present invention, when the thermoplastic polycaprolactone is impregnated with the mesh body, the polycaprolactone coated part of the polyethylene terephthalate fiber is melted, or the polycaprolactone fiber is melted with heat and then cooled, the mesh shaped body is stiffened by the polycaprolactone, which is attached to the outer portion of the thread, such that the shape can be maintained as it is, and even when an external force is applied from the outside, is not excessively stretched and easily returns to its original shape after being stretched to an appropriate length.

On the external circumferential surface of the core material 10, the structure 20 is formed so as to surround the core material 10, and here, the structure 20 is composed of the polycaprolactone composite that has polycaprolactone as the main component, and due to such a composition, may be firmly coupled with the polycaprolactone that is attached to the external circumferential surface of the thread. Consequently separation or peeling due to differences in the material between the core material 10 and the structure 20 is prevented.

Here, the structure 20 is formed so as to have a rectangular cross section of which the height is larger relative to the width such that sufficient rigidity is achieved with regard to an external force or impact.

Also, as described above, the structure 20 is composed of the polycaprolactone composite, and such a polycaprolactone composite is composed of polycaprolactone, which is the main component, and an additive composed of fiber reinforced glass fiber or polyethylene terephthalate fiber. The strength of the structure 20 is enhanced by such an additive, and thus, since the width of the structure 20 may be reduced, the fraction of a rhombus shaped air ventilation hole is increased to improve the air-permeability, and it also becomes possible for the structure 20 to be lightweight.

Moreover, polyethylene (PE) or polyurethane (PR) may also be added as an additive to the structure, and such polyethylene and polyurethane increases the time it takes for the structure 20 to be hardened and also improves the impact resistance such that sufficient time may be gained for the medical procedure of applying the cast on the affected area, and the structure also becomes robust with regard to external impact.

As described above, in the cast of the present invention, since the core material 10 is composed of thread, elongation in the lengthwise direction of each of the sides forming the rhombus is restricted, but deformation of the rhombus (for example, a shape in which the long diagonal of the rhombus becomes the short diagonal, and the short diagonal becomes the long diagonal) is easily achieved such that a medical procedure is easily performed on a body part, and since the core material 10 is surrounded with the structure 20 made of the polycaprolactone composite, structural integrity may be achieved such that the body is robustly supported.

An outer cover 30 may be formed/attached over the entire outer portion of the structure 20 or on an area thereof, and such an outer cover 30 is a rubber material and is formed through dipping, insert injection, or sheet fusion.

Figure 9:
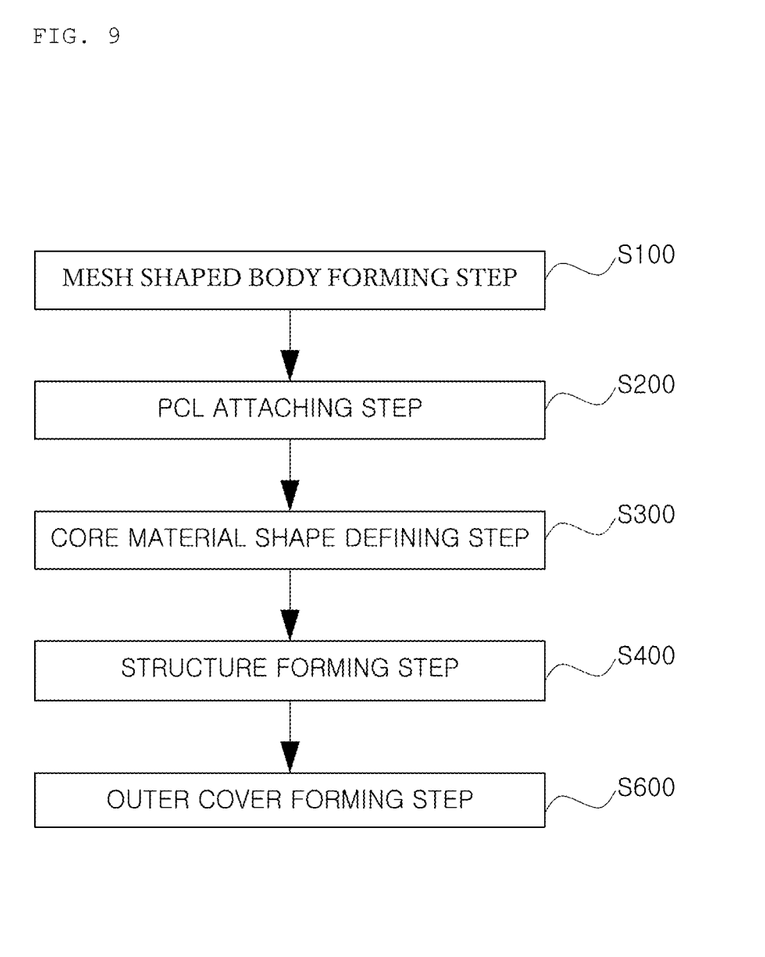
FIG. 9 is a production flow chart illustrating the steps in the production method for a thermoplastic cast of the present invention.

The cast (1) formed as such an above-described structure is produced through a mesh shaped body forming step S100, a polycaprolactone attaching step S200, a core material laying step S300, a structure forming step S400, and an outer cover forming step S500, and the like, as illustrated in FIG. 9. Hereinafter, detailed description is given for each of the steps.

(1) Mesh Shaped Body Forming Step S100

Figure 4:
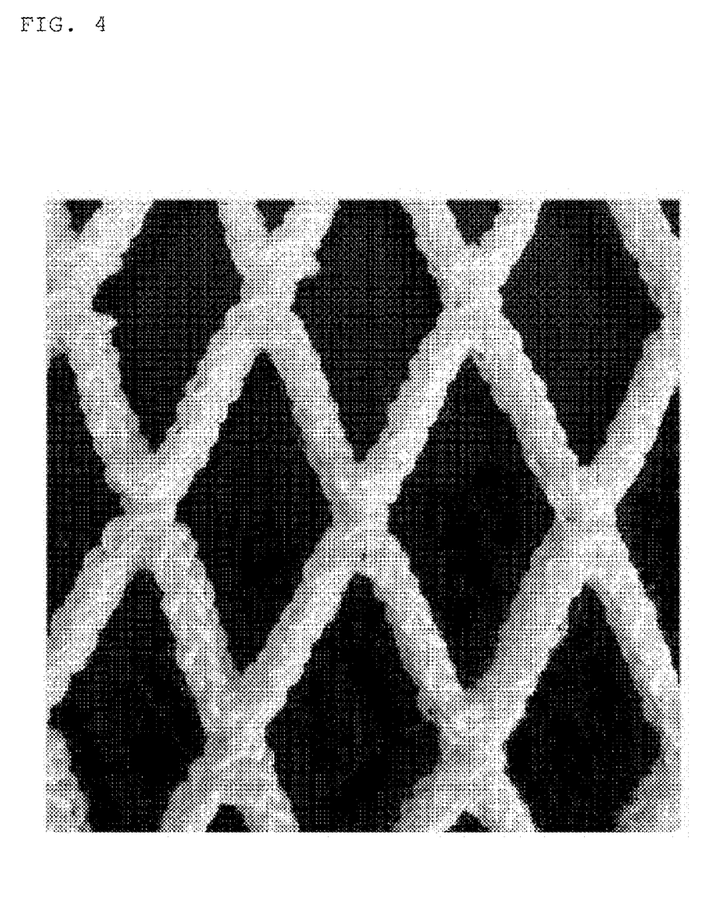
FIG. 4 is a photograph of an embodiment of a core material according to the present invention, produced in the shape of a mesh.

This step is the step for forming the mesh shaped by, as illustrated in FIG. 4, mutually crossing over and connecting threads having a predetermined diameter, and here, the thread used in forming the mesh shaped body is the thread composed of the common yarn, the blended yarn in which polyethylene terephthalate fiber and polycaprolactone fiber are mixed, or the polyethylene terephthalate fiber of which the external circumferential surface is coated with polycaprolactone, and thus the binding force with the structure 20 composed of the polycaprolactone composite is improved. Description thereof will be given later.

Also, it is desirable for the diameter of the thread, which forms the mesh shaped body while being in a state in which the plurality of strands of thin yarn are woven, to be 1~3 mm so as to have the appropriate strength and elasticity.

(2) Polycaprolactone Attaching Step S200

This step is the step for producing the core material 10, after the mesh shaped body composed of thread is produced through such an above-described mesh shaped body forming step S100, by placing such a mesh shaped body in a polycaprolactone impregnation tank to be impregnated with polycaprolactone, or by attaching polycaprolactone on the outer portion of the thread by applying heat to the mesh shaped body composed of the polyethylene terephthalate fiber of which the external circumferential surface is coated with polycaprolactone. Consequently, the strength of the core material 10 is improved while the core material 10 is able to maintain the form of the mesh shaped body such that the below-described structure forming step S400 may be easily performed.

In the present invention, one of three methods is selected as the method for attaching polycaprolactone to the outer portion of the thread to produce the core material 10. The first method is the method for attaching polycaprolactone to the outer portion of the thread by dipping and impregnating the mesh shaped body composed of thread in the polycaprolactone impregnation tank which is holding a polycaprolactone solution dissolved by a solvent and is maintained at a constant temperature. The second method is the method for attaching polycaprolactone to the outer portion of the thread by applying heat to the mesh shaped body in a state in which the mesh shaped body composed of polyethylene terephthalate fiber of which the external circumferential surface is coated with polycaprolactone is inserted in a heating device such as a microwave oven to thereby melt the polycaprolactone coated on the outer portion of the polyethylene terephthalate fiber, and this method has an advantage in that polycaprolactone is more uniformly attached over the entirety of the outer portion of the thread when compared to the previous method of attaching polycaprolactone on the outer portion of the thread through impregnation. The third method is the method for attaching polycaprolactone to the outer portion of the thread by applying heat to the mesh shaped body in a state in which the mesh shaped body formed from polyethylene terephthalate fiber and polycaprolactone fiber are inserted in a heating device such as a microwave oven to thereby melt the polycaprolactone fiber.

When polycaprolactone is attached to the outer portion of the thread through impregnation, the polycaprolactone solution used is that which is held in the polycaprolactone impregnation bath and diluted with a solvent such as tetrahydro furan (THF), and the like, and thus the polycaprolactone is dried while being easily percolated between the plurality of thin yarns forming the mesh shaped body such that the diameter of the mesh shaped body after being impregnated with polycaprolactone, that is, the cross section of the core material 10, is also uniform.

It is desirable for the cross-sectional diameter of the mesh shaped body (core material) to be 2~5 mm when the polycaprolactone composite is attached to the inner and outer portions of the mesh shaped body having a cross-sectional diameter of 1~3 mm, and this enables the core material 10 to have an appropriate stiffness when cooled through the below-described cooling step S300 such that the core shape 10 maintains the mesh shape when performing the subsequent structure forming step S400 and is thus easily handled, and allows a binding performance to be gained with the structure 20 which is composed of the polycaprolactone composite that surrounds the outer portion of the core material.

The polycaprolactone in the polycaprolactone composite attached to the outer portion of the thread is a thermoplastic resin that is easily softened in the temperature range of 55~80° C. and has non-adhesive and crystalline properties at room temperature, and thus when the polycaprolactone composite is cooled by being attached to the inner and outer portions of the mesh shaped as described above, the shape of the mesh shaped body can be maintained at room temperature.

(3) Core Material Shape Defining Step S300

This step is the step for shaping into a defined shape the core material 10, which is unable to be maintained in the form of the mesh shaped body when undergoing the process of impregnation, and the like, and is thus deformed into an arbitrary shape, and through this step, the core material 10 may be easily placed inside of a mold.

For example, in the case of attaching polycaprolactone on the outer portion of the thread through impregnation, when performing the polycaprolactone attaching step S200, after placing a solvent-diluted concentration of the polycaprolactone solution in the polycaprolactone impregnation bath which, as described above, is maintained in the temperature range of 40~60° C., the mesh shaped body is dipped in this polycaprolactone impregnation bath to thereby attach the polycaprolactone. During this process, the mesh shaped body may be unable to maintain the original shape and thus be deformed into an arbitrary shape, and in this case, it is not easy to insert the core material 10 into the mold used for attaching the structure 20 on the outer portion of the core material.

Figure 5:
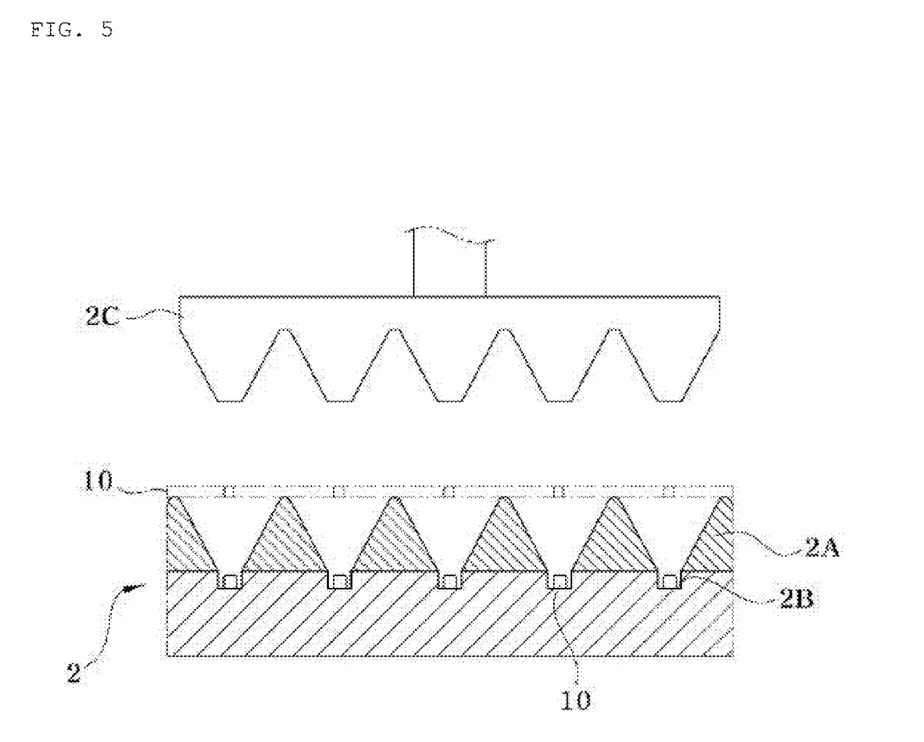
FIG. 5 is a use state diagram illustrating an embodiment in which a mold, a guide cap, and a pressure applying member are used according to the present invention.

To overcome this, in the present invention, before inserting the core material 10 inside of the mold, the shape of the core material 10, which was deformed into an arbitrary shape, is defined by applying pressure to, and inserting, the core material 10 in a shape template 2 in which is formed a groove in the shape of a defined mesh shaped body as illustrated in FIG. 5, and for this, the shape template is provided with a guide cap 2A, in which a plurality of guiding protrusions are formed protruding upwardly to have a mesh shape, and a pressure applying member 2C disposed above the guide cap 2A and applying pressure to, and thereby pushing, the core material 10 toward the groove 2B in the shape template. Due to such a configuration, when the core material 10 is first placed on the guide cap 2A and the pressure applying member 2C is then lowered toward the shape template 2, the shape is defined when the core material 10 placed on the guide cap 2A moves downward by sliding along the guiding protrusions of the guide cap 2A to be placed inside of the shape template, and thereby, the core material 10 can be easily placed in the mold for attaching the structure 20 on the outer portion of the core material.

Here, when the core material 10 to which is attached polycaprolactone on the outside thereof is stiffened, it may be very difficult to perform the shape defining operation, and thus in order to overcome this, it is desirable for the shape defining operation to be undertaken in a state in which flexibility is provided to the core material 10 by heating the core material 10 in a heater, and the like, before performing the shape defining operation.

(4) Structure Forming Step S400

This step is the step for inserting the core material having the defined shape in a mold for insert injection to form, by means of injection, the structure 20 composed of the polycaprolactone composite on the outer portion of the core material 10, so as to surround the core material 10.

Figure 6:
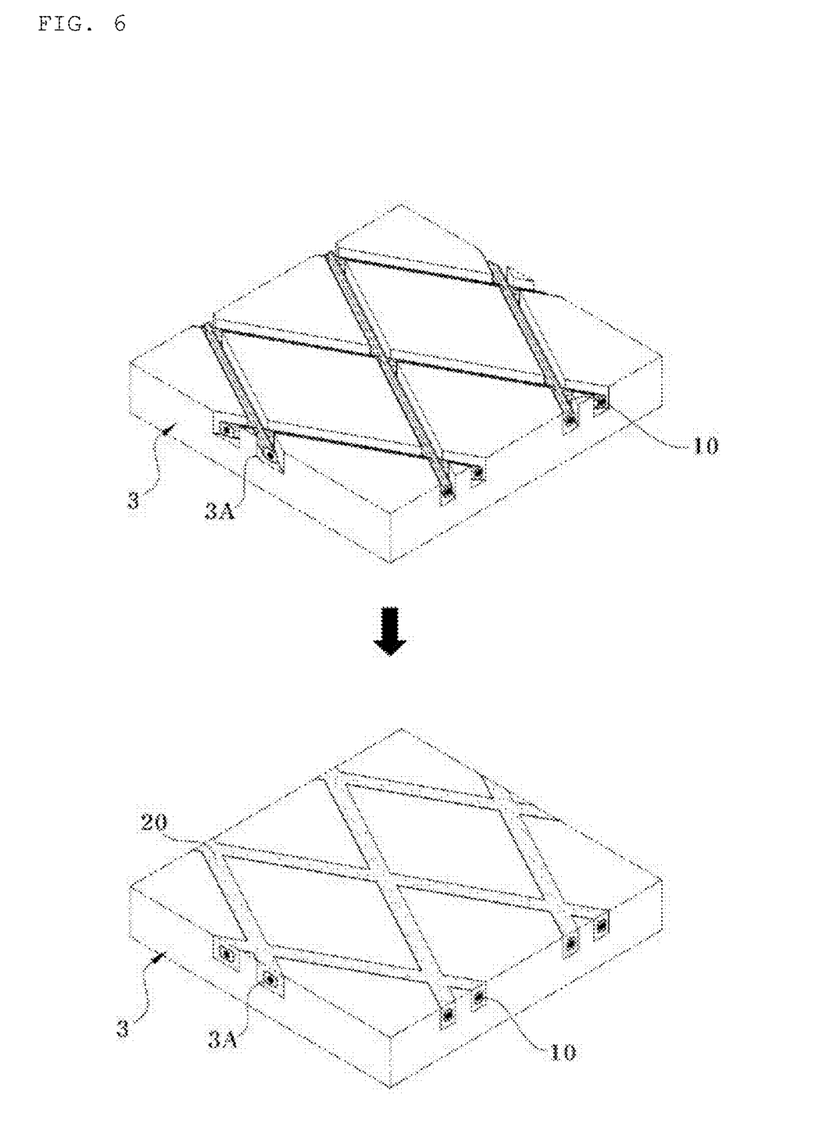
FIG. 6 is a schematic diagram illustrating an embodiment in which a structure is formed through insert injection by using a mold on the outer portion of a core material to which is attached polycaprolactone, according to the present invention.

When the core material 10 is defined in the shape of a mesh through the above core material shape defining step S300, this core material 10 having the defined shape is placed inside of the mold for insert injection to form, by means of injection, the structure 20, which is composed of the polycaprolactone composite, on the outer portion of the core material 10 so as to surround the core material 10. For this, as illustrated in FIG. 6, in the present invention, a mold 3, inside of which is formed the groove 3A which is made in the same shape as the shape of the mesh shaped body, composed of a top/bottom pair is prepared, and in a state in which the core material 10 is placed inside of the groove 3A of the mold 3, the polycaprolactone composite, of which the main component is polycaprolactone, is injected (insert injection) such that the structure 20 made of the polycaprolactone composite surrounds the external circumferential surface of the core material 10. Here, as described above, the structure 20 has polycaprolactone, which is the same material as the core material 10, as the main component, and an additive such as fiber reinforced glass fiber or polyethylene terephthalate fiber, and the like, is mixed therein to further improve the strength, and polyethylene or polyurethane is added in order to gain sufficient time to perform the medical procedure for applying the cast, while also improving the impact resistance.

Also, a nucleating agent including talc may be added to the polycaprolactone composite which forms the structure 20, and due to the addition of such a nucleating agent, crystallization of the polycaprolactone composite may be accelerated such that solidification of the polycaprolactone composite is quickly achieved during injection, and excessive crystallization of the polycaprolactone composite is prevented such that a uniform strength may be expected, and also the productivity is improved.

The structure 20 which is formed through insert injection on the outer portion of the core material 10 is formed so as to have a rectangular cross section of which the height is larger relative to the width such that sufficient rigidity may be gained with respect to an external force or impact. Here, the structure 20 is formed to have a width in the range of 5~6 mm and a height in the range of 5.5~6.5 mm, and thereby the cast having sufficient rigidity and flexibility may be realized. Also, since the structure 20 is formed through insert injection using the mold 3 which, as described above, has a smooth surface, the structure 20 having a smooth surface is produced.

Meanwhile, when the core material 10 is inserted and placed inside of the mold 3, the core material 10 may not be positioned in the center of the groove 3A formed in the mold 3 and instead be positioned toward one side or toward the bottom of the mold 3, and in this case, there is a concern that the polycaprolactone formed on the outer portion of the core material may not be formed to a uniform thickness, and thus it is desirable to form a spacer (not shown) in the shape of a protrusion in the groove 3A which is formed inside of the mold 3 such that the core material 10 may be positioned in the center of the groove 3A in the mold 3.

Also, when the cast is applied to the affected area of the patient, according to the part on which the cast is applied, there may be a portion of the mesh shaped cast which is deformed to a greater degree relative to the other portions, and in this case, the portion at which the structures 20 mutually cross each other may not be realized as a flat surface and instead protrude in an upward or downward direction, and when protruding in a downward direction, the protruding portion may press the skin of the patient such that the patient feels discomfort. Thus, in the present invention, in order to prevent this, when forming the structure 20, an inwardly recessed groove is formed in the portion at which the mesh shaped structures 20 cross over with each other, or the thickness of the portion at which the structures 20 cross over with each other is formed to be relatively thinner, and here, the recessed groove may be formed by forming a protruding portion (not shown) in the mold 3 for forming the structure 20, and the structure of which the crossing portion of the structure 20 is relatively thinner may be realized by making the thickness of the portion in the mold which forms this portion relatively thinner.

As above, in the present invention, since the structure 20 is formed using the mold through insert injection, the structure 20 having a uniform thickness may be quickly formed and is thus easily mass produced, and also, since by attaching polycaprolactone on the outer portion of the thread, the core material 10 having an unevenly shaped surface is surrounded by the structure 20 having a smooth surface, the discomfort felt by the patient may be relieved even when the cast 1 contacts the skin of the patient.

(5) Other Cover Forming Step S500

This step is the step for forming the outer cover 30 on the outer portion of the structure 20, and this step may be selectively performed as needed.

By passing through the above structure forming step S400, the cast 1 having the smooth surface is produced and thus even when contacting the skin of the patient, the patient does not feel discomfort. However, since the structure 20 becomes hard after the cast is applied on the affected area of the patient and then cooled, the patient may feel discomfort, and thus, in the present invention, the outer cover 30 made of a rubber material may be further formed on the structure 20 to relieve the discomfort of the patient, and here, the outer cover 30 may be formed through the below two methods.

Figure 7A:
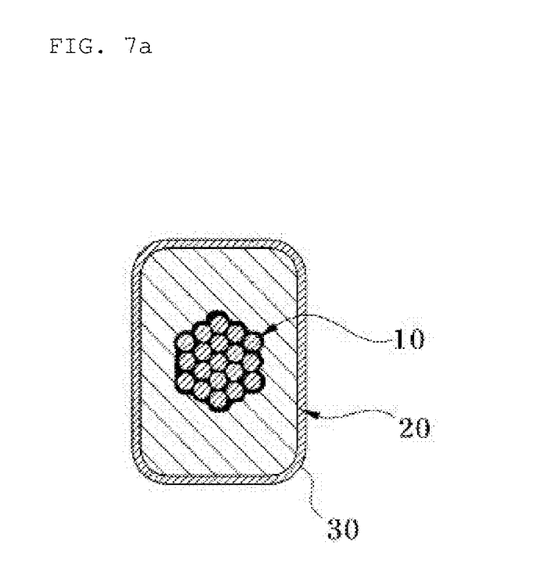
FIGS. 7A and 7B are cross-sectional views illustrating an embodiment in which an outer cover is formed on a structure according to the present invention.

As illustrated in FIG. 7A, the first method is the method for forming the outer cover 30 made of the rubber material on the entirety of all four surfaces of the structure 20, and here, the outer cover 30 is formed by dipping and then undipping the entirety of the structure 20 in a storage tank which holds a mixed solution of a binder and a rubber solution (dipping), by placing the structure 20 inside of the mold, such as in the structure forming step S400, and inserting the rubber which is in a liquid state on the external circumferential surface thereof (insert injection), or by installing a sheet made of rubber material on the outer portion of the structure 20 and then using heat to fuse the sheet made of rubber material to the structure 20 (sheet fusion).

Figure 7B:
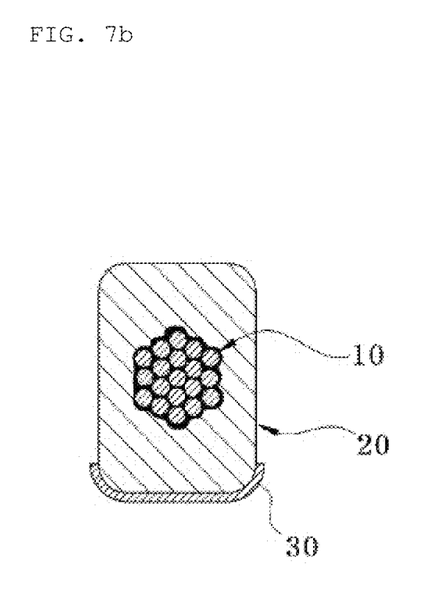

As illustrated in FIG. 7B, the second method is the method for forming the outer cover 30 on only the bottom surface of the structure 20, and here, among the four surfaces of the structure, only the bottom surface which contacts the skin of the patient is dipped in the storage tank that holds the mixed solution of binder and rubber solution and then undipped to form the outer cover 30, and when the outer cover 30 formed on the bottom surface of the structure 20 is formed in the shape of protrusions, ventilation may thereby be achieved.

When the outer cover 30 made of the rubber material is formed, such as above, on the cast 1 of the present invention, the outer cover 30 acts as a cushioning material such that even when the cast directly contacts the skin of the patient, the pressure applied on the skin is reduced, and consequently the generation of pain due to pressure from the cast is prevented, and also, it is not necessary to install a separate skin protector, and the like, on the bottom of the cast 1.

Figure 8:
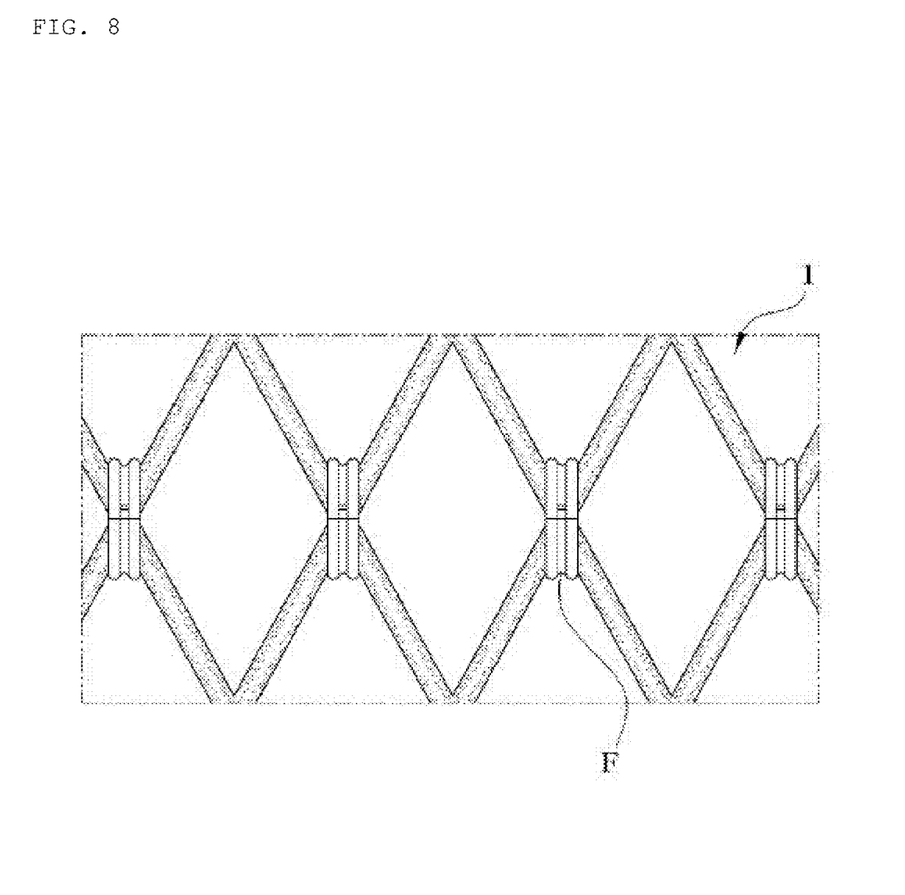
FIG. 8 is a use state diagram illustrating an embodiment of a fixing member installed in a thermoplastic cast according to the present invention.

When applying the thermoplastic cast 1 of the present invention, which is formed to have a structure such as described above, on the affected area of the patient, the cast 1 which is at room temperature is first softened by heating in a heating device such as a hot water heater or a microwave oven and is thereby made into a freely deformable state, and then, after being applied so as to surround the affected area of the patient which is fractured or needs correcting, the cast 1 is gradually cooled to room temperature in a state in which both ends of the cast which are in contact with each other, are fixed by the cast 1 using a fixing member F as illustrated in FIG. 8, and thereby solidified to complete the application of the cast 1.

Here, the fixing member F used for fixing both ends of the cast may be one of any configuration, including a clip-type or a buckle-type, that fixes both ends of the cast 1, but in order to allow an x-ray examination, and the like, to be performed while the cast 1 is being worn, is desirably made of a plastic material, instead of a metal material.

Also, when it is necessary for the cast 1 to be removed from the affected area of the patient or be corrected, the cast may be removed from the affected area merely by removing the fixing member F installed on both ends and then spreading apart both ends of the cast 1, and thus disassembly is comparatively simple. Also, when reapplying the cast 1 to the affected area of the patient, the disassembled cast 1 may be reheated and softened, and then easily modified or reapplied by once again going through the above-described process for applying the cast 1.

As described above, in the present invention the cast is formed to be mesh shaped such that ventilation is improved, and since the structure composed of the polycaprolactone composite is formed through insert injection so as to surround the outer portion of the core material, the cast is structurally robust while at the same time the patient does not feel discomfort, and since the structure is composed of thermoplastic material, the cast has the advantage of being able to be modified or reused as needed.

The invention claimed is:

1. A thermoplastic cast for covering and fixing the body such as a fractured part of a patient, the thermoplastic cast comprising:
   a structure configured to cover at least a part of the fractured part of the patient, wherein:
      the structure includes a thermoplastic resin such that the structure can be deformed to conform the part of the fractured part by heating,
      the structure is formed as a mesh shaped body having a plurality of rhombus shaped air ventilation holes,
      the thermoplastic cast further comprises a core material for supporting the structure; and
      the core material defines a limit of deformation of the structure when the structure becomes plastic by heating,
      the core material has a thinner thickness than the structure and have a mesh shape,
      the core material is stretched when an external force is applied to the core material and returns to original shape when the external force is not applied to the core material, and
      the core material is deformable to a shape in which a long diagonal of at least one of the plurality of rhombus shaped air ventilation holes becomes a short diagonal of the at least one of the plurality of rhombus shaped air ventilation holes, and wherein the short diagonal of the at least one of the plurality of rhombus shaped air ventilation holes becomes the long diagonal of the at least one of the plurality of rhombus shaped air ventilation holes, and
      the core material configured to restrict the elongation of the structure in the lengthwise direction of each of the sides forming the at least one of the plurality of rhombus shaped air ventilation holes.

2. The thermoplastic cast of claim 1, wherein the structure is formed so as to have a cross section of which a height is larger relative to a width such that sufficient rigidity may be gained with respect to an external force or impact.

3. The thermoplastic cast of claim 1, wherein the structure includes a polycaprolactone composite.

4. The thermoplastic cast of claim 3, wherein a fiber reinforced glass fiber or a polyethylene terephthalate fiber is added to the polycaprolactone composite.

5. The thermoplastic cast of claim 3, wherein a polyethylene or a polyurethane is added to the polycaprolactone composite.

6. The thermoplastic cast of claim 3, wherein a nucleating agent made of a talc is added to the polycaprolactone composite.

7. The thermoplastic cast of claim 1, wherein:
   the core material is obtained by weaving a plurality of strands of thin yarn, and the core material includes polycaprolactone attached to the strands.

* * * * *